(12) United States Patent
Tai et al.

(10) Patent No.: US 8,805,542 B2
(45) Date of Patent: Aug. 12, 2014

(54) PARYLENE-BASED MICROELECTRODE ARRAY IMPLANT FOR SPINAL CORD STIMULATION

(71) Applicants: California Institute of Technology, Pasadena, CA (US); The Regents of the University of California, Oakland, CA (US); University of Louisville Research Foundation, Inc., Louisville, KY (US)

(72) Inventors: Yu-Chong Tai, Pasadena, CA (US); Mandheerej S. Nandra, Pasadena, CA (US); Joel W. Burdick, Pasadena, CA (US); Damien Craig Rodger, South Pasadena, CA (US); Andy Fong, Los Angeles, CA (US); Victor Reggie Edgerton, Los Angeles, CA (US); Roland R. Roy, Playa Vista, CA (US); Yury Gerasimenko, Los Angeles, CA (US); Igor Lavrov, Rancho Palos Verdes, CA (US); Susan J. Harkema, Louisville, KY (US); Claudia A. Angeli, Louisville, KY (US)

(73) Assignees: California Institute of Technology, Pasadena, CA (US); University of Louisville Research Foundation, Inc., Louisville, KY (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/946,338

(22) Filed: Jul. 19, 2013

(65) Prior Publication Data
US 2013/0310911 A1    Nov. 21, 2013

Related U.S. Application Data

(63) Continuation of application No. PCT/US2012/022257, filed on Jan. 23, 2012.

(60) Provisional application No. 61/435,188, filed on Jan. 21, 2011.

(51) Int. Cl.
*A61N 1/05*    (2006.01)

(52) U.S. Cl.
CPC ............ *A61N 1/0551* (2013.01); *A61N 1/0553* (2013.01); *A61N 1/0558* (2013.01)
USPC .......................................... 607/117; 607/116

(58) Field of Classification Search
CPC . A61N 1/0551; A61N 1/0529; A61N 1/0553; A61N 1/0476; A61B 2562/125; A61B 2562/046
USPC .................................................. 607/116, 117
See application file for complete search history.

(56) References Cited

U.S. PATENT DOCUMENTS

| | | | |
|---|---|---|---|
| 2003/0032992 A1 | 2/2003 | Thacker | |
| 2006/0089696 A1* | 4/2006 | Olsen et al. | 607/122 |
| 2007/0265691 A1 | 11/2007 | Swanson | |
| 2008/0046049 A1 | 2/2008 | Skubitz et al. | |
| 2008/0221653 A1 | 9/2008 | Agrawal | |
| 2009/0299166 A1* | 12/2009 | Nishida et al. | 600/378 |
| 2009/0299167 A1* | 12/2009 | Seymour | 600/393 |

FOREIGN PATENT DOCUMENTS

| | | |
|---|---|---|
| WO | 2009/111142 A2 | 9/2009 |
| WO | 2010/114998 A1 | 10/2010 |
| WO | 2012/100260 A2 | 7/2012 |

OTHER PUBLICATIONS

International Search Report for International Application No. PCT/US2012/022257 filed on Jan. 23, 2012.
Nandra et al., A parylene-based microelectrode array implant for spinal cord stimulation in rats. Conf. Proc. IEEE Eng. Med. Biol. Soc., pp. 1007-1010 (2011).
Rodger et al., High density flexible parylene-based multielectrode arrays for retinal and spinal cord stimulation. Proc. of the 14th International Conference on Solid-State Sensors, Actuators and Microsystems, pp. 1385-1888 (2007).
Extended European Search Report for European Application No. 12736491.7 issued on May 20, 2014.

* cited by examiner

Primary Examiner — Christopher D Koharski
Assistant Examiner — Michael Carey
(74) Attorney, Agent, or Firm — K&L Gates LLP; Louis C. Cullman; Brian J. Novak (57) ABSTRACT

An implantable electrode array assembly configured to apply electrical stimulation to the spinal cord. A substantially electrically nonconductive layer of the device has a first portion positionable alongside the spinal cord that includes a plurality of first openings and a second portion that includes a plurality of second openings. Electrodes and traces are positioned inside a peripheral portion of a body portion of the device and alongside the layer. At least one of the first openings is adjacent each of the electrodes to provide a pathway through which the electrode may provide electrical stimulation to the spinal cord. At least one of the second openings is adjacent each of the traces to provide a pathway through which the trace may receive electrical stimulation. At least one trace is connected to each electrode and configured to conduct electrical stimulation received by the trace(s) to the electrode.

21 Claims, 9 Drawing Sheets

PARYLENE-BASED MICROELECTRODE ARRAY IMPLANT FOR SPINAL CORD STIMULATION

CROSS REFERENCE TO RELATED APPLICATION(S)

This application is a continuation of International Application PCT/US2012/22257, filed Jan. 23, 2012, and that International Application was published under PCT Article 21(2) in English. This application also claims the benefit of U.S. Provisional Application No. 61/435,188, filed Jan. 21, 2011, which is incorporated herein by reference in its entirety.

STATEMENT REGARDING FEDERALLY SPONSORED RESEARCH OR DEVELOPMENT

This invention was made with Government support under Grant No. W81XWH-09-2-0024, awarded by the United States Army, Medical Research and Materiel Command; and Grant No. EB076151, awarded by the National Institutes of Health. The Government has certain rights in this invention.

BACKGROUND OF THE INVENTION

1. Field of the Invention

The present invention is directed generally to implantable electrode arrays, and more particularly to implantable electrode arrays used to deliver electrical stimulation to the spinal cord.

2. Description of the Related Art

Spinal cord injuries are estimated to afflict over 1.3 million individuals in the United States alone, and paralysis is estimated to affect over 5 million individuals. See "One Degree of Separation: Paralysis and Spinal Cord Injury in the United States," Christopher and Dana Reeve Foundation (2009). The debilitating nature of paralysis has a profound effect on quality of life, making even partially effective treatments highly desirable goals for the scientific community.

Fortunately, experimental research on animals has shown that some level of recovery of locomotion is possible. In particular, epidural spinal cord stimulation has been shown to induce stepping in rats. See R. M. Ichiyama, G. Courtine, Y. P. Gerasimenko, G. J. Yang, R. Brand, I. Lavrov, H. Zhong, R. Roy, V. R. Edgerton, "Step Training Reinforces Specific Spinal Locomotor Circuitry in Adult Spinal Rats", *J. Neuroscience*, vol. 29, pp. 7370-7375 (2008); and R. M. Ichiyama, Y. P. Gerasimenko, H. Zhong, R. R. Roy, V. R. Edgerton, "Hindlimb stepping movements in complete spinal rats induced by epidural spinal cord stimulation," *Neuroscience Letters*, vol. 383, issue 3, pp. 339-344 (2005). In these studies, rats were implanted with up to eight wire electrodes. The implanted wire electrodes each extended from a headplug down the neck and to the spinal cord of the rat. During testing, each of the rats was suspended in a jacket such that its hind limbs were positioned on a treadmill. About two weeks after the spinal cord injury, clear stepping patterns were evident when the spinal cord was stimulated. This suggested that the electrical stimulation activated a central pattern generator in the spinal cord.

The following publications provide examples of work related to electrode arrays used to apply electrical stimulation to the spinal cord: D. C. Rodger, W. Li, A. J. Fong, H. Ameri, E. Meng, J. W. Burdick, R. R. Roy, V. Reggie Edgerton, J. D. Weiland, M. S. Humayun, Y. C. Tai, "Flexible microfabricated parylene multielectrode arrays for retinal stimulation and spinal cord field modulation," *Proc. 4th International IEEE-EMBS Special Topic Conference on Microtechnologies in Medicine and Biology*, Okinawa, Japan, pp. 31-34 (2006); K. W. Meacham, R. J. Giuly, L. Guo, S. Hochman, S. P. DeWeerth, "A lithographically-patterned, elastic multi-electrode array for surface stimulation of the spinal cord", *Biomedical Microdevices*, vol. 10, no. 2, pp 259-269 (2008); and D. C. Rodger, Wen Li, H. Ameri, A. Ray, J. D. Weiland, M. S. Humayun, Y. C. Tai, "Flexible Parylene-based Microelectrode Technology for Intraocular Retinal Prostheses," *Proc. IEEE-NEMS 2006*, pp 743-746 (2006).

The publications cited above and other work has led to various designs for high-density electrode arrays to further research, but unfortunately none of these designs has been successfully implanted chronically. A need exists for a chronic implant because chronic implantation is necessary for many applications, such as conducting research, helping a patient move (e.g., step, stand, grip, and the like), improving control of voluntary functions (e.g., voiding the bladder), improving functionality of autonomic processes (e.g., temperature control), and the like. A need also exists for an electrode array assembly configured to more accurately deliver electrical signals to selected locations along the spinal cord. The present application provides these and other advantages as will be apparent from the following detailed description and accompanying figures.

SUMMARY OF THE INVENTION

Embodiments of the invention include an implantable device configured to apply electrical stimulation to a spinal cord of a subject (e.g., a human being or other mammal, such as a rat). The device includes a body portion and a first layer. The body portion has a peripheral portion. Optionally, the peripheral portion includes a frame positioned adjacent the first layer. The frame may be constructed from one or more layers of a substantially electrically nonconductive material (e.g., parylene-A, parylene-C, parylene-AM, parylene-F, parylene-N, parylene-D, and the like). The first layer is constructed from a substantially electrically nonconductive material. In some embodiments, the first layer is constructed from at least one of parylene-A, parylene-C, parylene-AM, parylene-F, parylene-N, and parylene-D. The first layer has a first portion and a second portion. The first portion is positionable alongside the spinal cord and includes a first plurality of openings. For example, the first portion of the first layer may be positioned against a dura of the spinal cord and the device configured to provide electrical stimulation to the dura. The second portion includes a second plurality of openings.

A plurality of electrodes is positioned inside the peripheral portion and alongside the first portion of the first layer. At least one of the first plurality of openings is adjacent each of the electrodes to provide a pathway through which the electrode may provide electrical stimulation to the spinal cord when the first portion is positioned alongside the spinal cord. In some embodiments, more than one of the first plurality of openings is adjacent each of the plurality of electrodes. In embodiments in which the first portion of the first layer is to be positioned against the dura of the spinal cord, the plurality of electrodes is configured to provide electrical stimulation to the dura.

A plurality of traces is positioned inside the peripheral portion and alongside the first layer with at least one of the second plurality of openings being adjacent each of the traces to provide a pathway through which the trace may receive electrical stimulation. One or more of the traces is/are connected to each of the electrodes and configured to conduct electrical stimulation received by the one or more of the traces to the electrode. In some embodiments, two of the traces are connected to each of the electrodes. In particular embodiments, the plurality of traces are configured to conduct different electrical stimulation to different ones of the plurality of electrodes. Further, the plurality of traces may be configured to conduct electrical stimulation to fewer than all of the plurality of electrodes.

In some embodiments, the first layer includes a plurality of grid structures with a different one of the grid structures adjacent each of the plurality of electrodes. Each grid structure defines a plurality of cells. For each of the plurality of electrodes, each of the at least one of the first plurality of openings adjacent the electrode is positioned inside a different one of the cells of the grid structure adjacent the electrode.

In some embodiments, the body portion includes a second layer. In such embodiments, the plurality of electrodes and the plurality of traces may be positioned between the first and second layers. The first and second layers may each be constructed from at least one of parylene-A, parylene-C, parylene-AM, parylene-F, parylene-N, and parylene-D. Optionally, a flexible outer coating may coat at least a portion of the second layer of the body portion and a portion of the first layer between the first portion of the first layer and the second portion of the first layer. The outer coating may include at least one of a biomedical grade epoxy and a silicone elastomer.

Embodiments also include a method of constructing an implantable electrode array assembly configured to apply electrical stimulation to the spinal cord of a subject (e.g., a human being or other mammal, such as a rat). The method includes forming a patterned layer of electrically conductive material defining a plurality of electrodes and a plurality of traces, at least one trace being connected to each of the plurality of electrodes. The method also includes forming a first layer of a substantially electrically nonconductive material adjacent the patterned layer. The method also includes forming (e.g., etching) a plurality of first openings and a plurality of second openings in the first layer. The first openings provide access to the plurality of electrodes through the first layer. A different grid defining portion of the first openings is adjacent each of the electrodes. Each grid defining portion exposes a plurality of contacts of the electrode to which the grid defining portion is adjacent. The plurality of second openings provide access to the plurality of traces through the first layer.

In particular embodiments, the method further includes positioning a sacrificial layer (e.g., a layer of photoresist material) on a substrate (e.g., a silicon wafer), forming a second layer of a substantially electrically nonconductive material on the sacrificial layer, and removing the sacrificial layer to thereby release the second layer from the substrate. In such embodiments, the patterned layer is positioned on the second layer. The patterned layer may be formed on the second layer using a metal deposition technology (e.g., ebeam evaporation). Optionally, the method may include forming a frame layer on the substrate. In such embodiments, the frame layer is underneath the second layer and at least partially defines a frame around the patterned layer. The first and second layers may each be constructed from at least one of parylene-A, parylene-C, parylene-AM, parylene-F, parylene-N, and parylene-D. The first and second layers may be formed from the same material. Optionally, the method may include applying a coating to at least a portion of the second layer and at least a portion of the first layer.

Another embodiment includes a system that includes a stimulation generator, an implantable electrode array assembly, a baseplate, and a plurality of wires. The stimulation generator is configured to generate electrical stimulation. The implantable electrode array assembly has a proximal end portion connectable to at least one vertebrae and a distal end portion positionable along the spinal cord. The proximal end portion has a plurality of electrical connections to a plurality of electrodes positioned on the distal end portion. The baseplate is configured to be connected to the at least one vertebrae and to connect the assembly to the at least one vertebrae. The plurality of wires is connected to the baseplate and the stimulation generator. The plurality of wires is configured to conduct electrical stimulation generated by the stimulation generator to the baseplate. The baseplate is configured to conduct the electrical stimulation to the plurality of electrical connections of the proximal end portion of the assembly. Optionally, the system may include an overhanging portion connected to the baseplate and positioned to overhang at least a portion of the proximal portion of the assembly to help protect the assembly from external moving tissue.

DETAILED DESCRIPTION OF THE INVENTION

Figure 1:
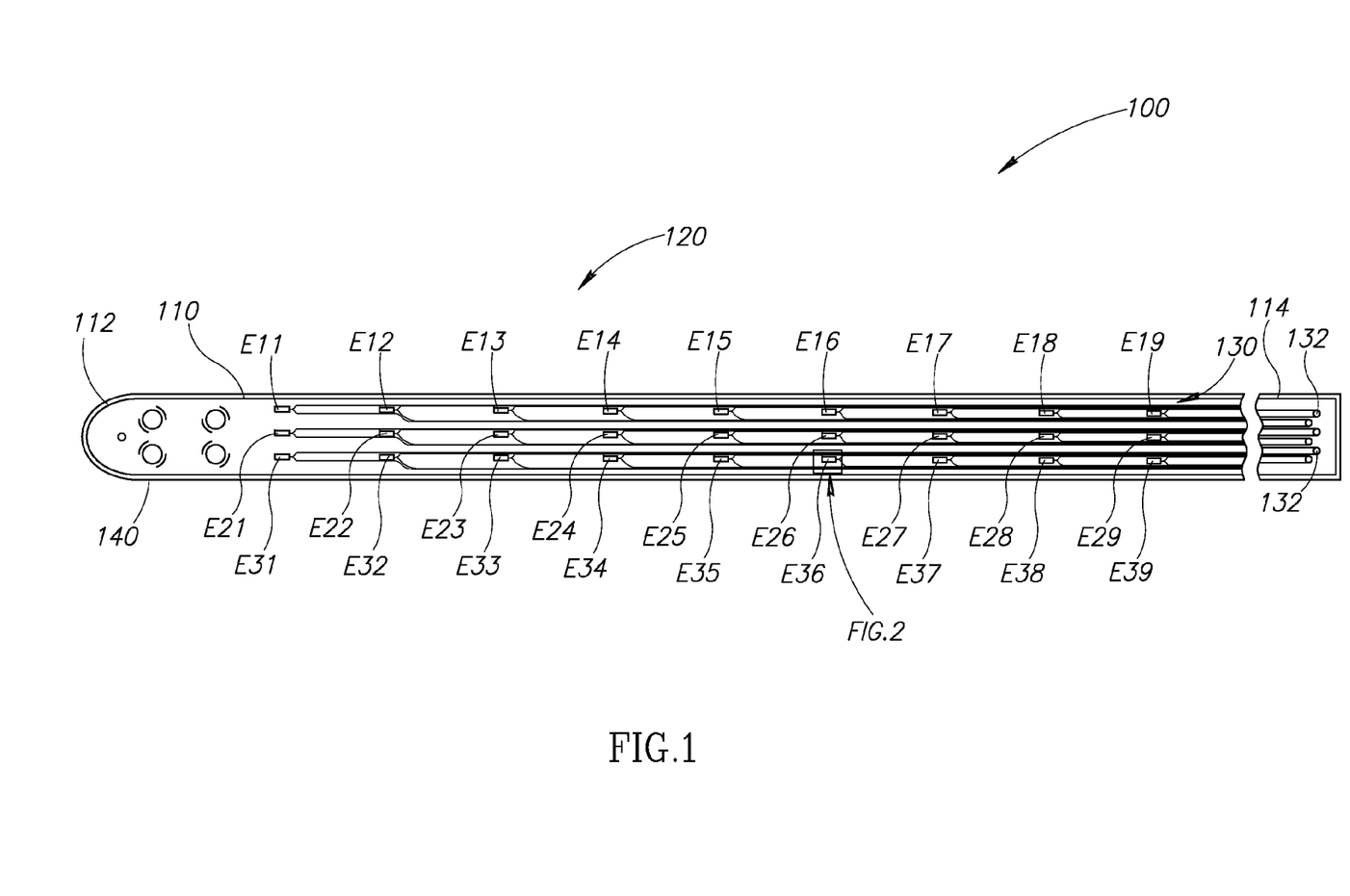
FIG. 1 is a view of an underside of an implantable electrode array assembly.

FIG. 1 illustrates an implantable electrode array assembly 100. While the embodiment of the assembly 100 illustrated is configured for implantation in a rat 500 (see FIG. 5A), embodiments may be constructed for use in other subjects, such as other mammals, including humans, and such embodiments are within the scope of the present teachings. The assembly 100 is for use with a subject that has a spinal cord 330 (see FIG. 3) with at least one selected spinal circuit (not shown) and a neurologically derived paralysis in a portion of the subject's body. By way of a non-limiting example, the assembly 100 may be implanted epidurally along the spinal cord 330. The assembly 100 may be positioned at one or more of a lumbosacral region, a cervical region, and a thoracic region of the spinal cord 330.

By way of non-limiting examples, when activated, the selected spinal circuit may (a) enable voluntary movement of muscles involved in at least one of standing, stepping, reaching, grasping, voluntarily changing positions of one or both legs, voiding the subject's bladder, voiding the subject's bowel, postural activity, and locomotor activity; (b) enable or improve autonomic control of at least one of cardiovascular function, body temperature, and metabolic processes; and/or (c) help facilitate recovery of at least one of an autonomic function, sexual function, vasomotor function, and cognitive function. Without being limited by theory, it is believed that the selected spinal circuit has a first stimulation threshold representing a minimum amount of stimulation required to activate the selected spinal circuit, and a second stimulation threshold representing an amount of stimulation above which the selected spinal circuit is fully activated and adding the induced neurological signals has no additional effect on the at least one selected spinal circuit.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Alzheimer's, ischemia, stroke, amyotrophic lateral sclerosis (ALS), primary lateral sclerosis (PLS), and cerebral palsy.

If the paralysis was caused by a spinal cord injury at a first location along the spinal cord 330, the assembly 100 may be implanted (e.g., epidurally) at a second location below the first location along the spinal cord relative to the subject's brain (not shown).

The assembly 100 is configured to apply electrical stimulation to a portion of a spinal cord 330 of the subject. The electrical stimulation may include at least one of tonic stimulation and intermittent stimulation. The stimulation applied may be pulsed. The electrical stimulation may include simultaneous or sequential stimulation of different regions of the spinal cord. The electrical stimulation applied by the assembly 100 may be below the second stimulation threshold such that the at least one selected spinal circuit is at least partially activatable by the addition of signals generated by the subject. By way of a non-limiting example, such subject generated signals may be induced by subjecting the subject to physical activity or training (such as stepping on a treadmill). These signals may be induced in a paralyzed portion of the subject. By way of another non-limiting example, the subject generated signals may include supraspinal signals.

Figure 2:
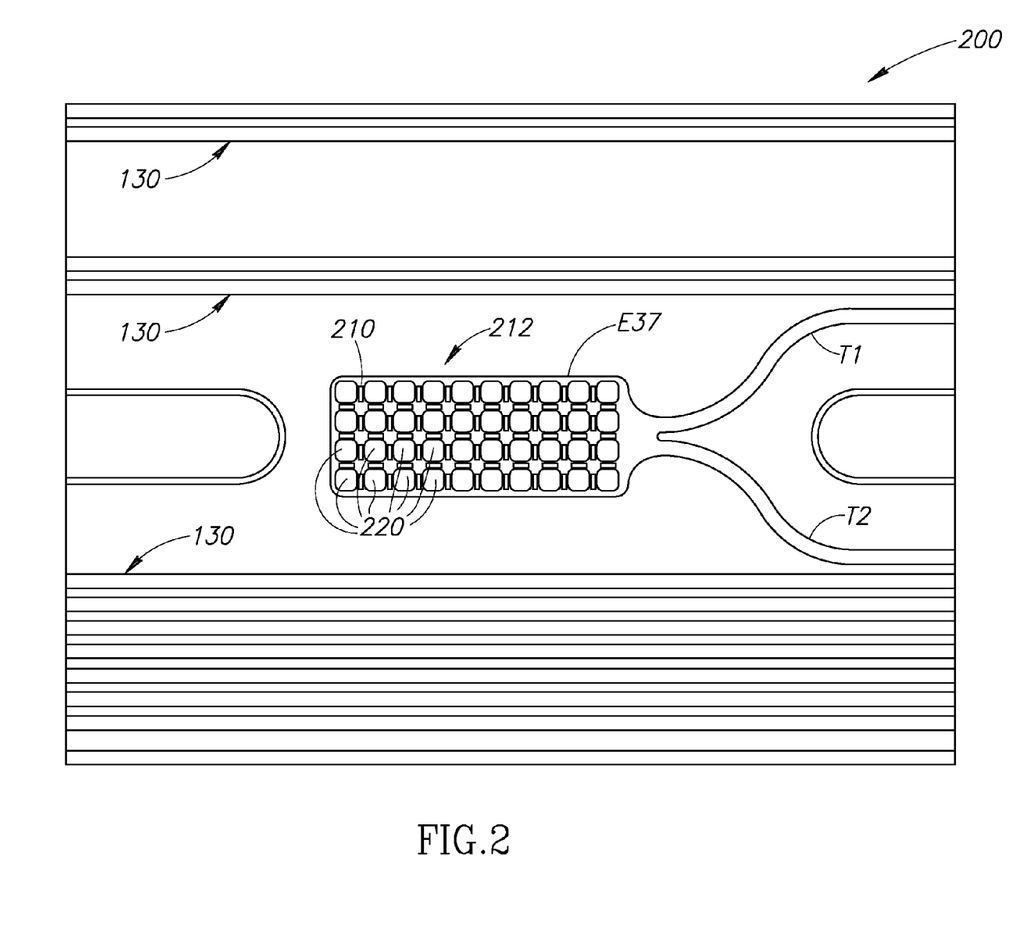
FIG. 2 is an enlarged view of a portion of the assembly of FIG. 1.
Figure 3:
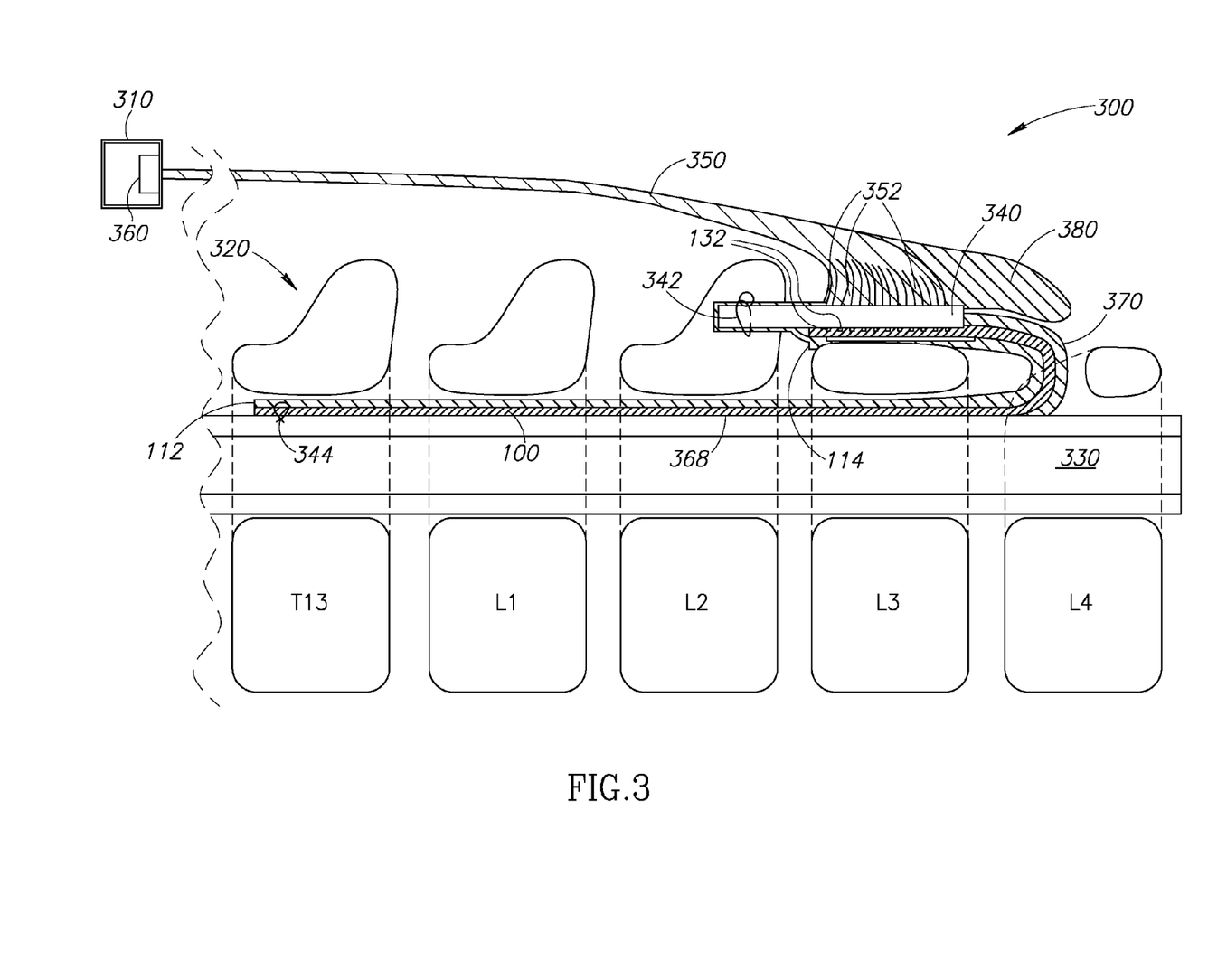
FIG. 3 is a cross-sectional view of a cable system incorporating the assembly of FIG. 1 implanted in a rat.
Figure 5A:
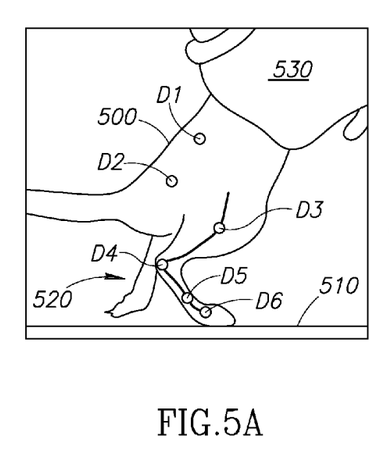
FIG. 5A is an illustration of a spinalized rat implanted with the assembly of FIG. 1 suspended above a treadmill and a portion of a motion capture system used to record stepping motion of the rat on the treadmill.

As mentioned above, the embodiment of the assembly 100 illustrated in FIGS. 1-3 is configured for implantation in the rat 500 (see FIG. 5A). Thus, the embodiment of the assembly 100 illustrated is sized (e.g., about 59 mm by about 3 mm) and shaped for implantation into the rat 500. However, through application of ordinary skill in the art to the present teachings, embodiments may be constructed for use with other subjects, such as other mammals, including humans.

FIG. 2 illustrates an enlarged portion 200 of the assembly 100 depicted in FIG. 1. The assembly 100 may be characterized as being a microelectromechanical systems ("MEMS") device. As mentioned above, the assembly 100 is configured for implantation along the spinal cord 330 (see FIG. 3) and to provide electrical stimulation thereto. For example, the assembly 100 may provide epidural stimulation to the spinal cord 330. The assembly 100 allows for a high degree of freedom and specificity in selecting the site of stimulation compared to prior art wire-based implants, and triggers varied biological responses that can lead to an increased understanding of the spinal cord 330 and locomotion recovery for victims of spinal cord injury.

Turning to FIG. 1, the assembly 100 includes a body portion 110, an electrode array 120, and a plurality of electrically conductive traces 130. The body portion 110 includes a distal end portion 112, a proximal end portion 114 (opposite the distal end portion), a frame 140, and a grid structure 210 (see FIG. 2) for each electrode E11-E19, E21-E29, and E31-E39 of the electrode array 120. Each of the grid structures 210 defines a plurality of cells 212. By way of a non-limiting example, the grid structures 210 may each be constructed from parylene (e.g., parylene-C). In the embodiment illustrated, the grid structure 210 includes 40 cells.

As mentioned above, the electrode array 120 includes the plurality of electrodes E11-E19, E21-E29, and E31-E39 (e.g., 9×3 electrodes). The electrodes E11-E19, E21-E29, and E31-E39 are arranged in a two-dimensional array. Each of the electrodes E11-E19, E21-E29, and E31-E39 includes a plurality of electrically conductive contacts 220. The contacts 220 are sites at which the electrode (e.g., the electrode E37 illustrated in FIG. 2) will contact the spinal cord (e.g., the dura). The contacts 220 are in electrically communication with one another. The embodiment of the electrode E37 illustrated includes 40 contacts 220. However, this is not a requirement. As mentioned above, each of the electrodes E11-E19, E21-E29, and E31-E39 corresponds to a unique one of the grid structures 210. In the embodiment illustrated, for each of the electrodes E11-E19, E21-E29, and E31-E39, each of the contacts 220 is positioned within a different one of the cells 212 of the corresponding grid structure 210. The grid structure 210 may help prevent delamination of the layers of the assembly 100 (see FIG. 1). As is apparent to those of ordinary skill in the art and as will be explain below, the grid structure 210 and contacts 220 may be formed by selectively etching a layer of substantially electrically non-conductive material (e.g., parylene) adjacent a pad of electrically conductive material (e.g., metal) to define the grid structure 210 and expose portions of the electrically conductive material within the cells 212 of the grid structure to define the contacts 220.

While the electrode array 120 illustrated includes 27 electrodes, in other embodiments, the number of electrodes may range from one electrode to about 100,000 electrodes or more. In certain embodiments, the electrode array 120 includes at least 10, at least 15, at least 20, at least 25, at least 50, at least 100, at least 250, at least 500, or at least 1000 electrodes. In various embodiments, the interelectrode spacing of adjacent electrodes in the electrode array 120 varies from about 100 µm or about 500 µm, or about 1000 µm or about 1500 µm to about 2000 µm, or about 3000 µm, or about 4000 µm, or about 4500 µm, or about 5000 µm. In various embodiments, interelectrode spacing ranges from about 100 µm, about 150 µm, about 200 µm, or about 250 µm up to about 1,000 µm, about 2000 µm, about 3000 µm, or about 4,000 µm. In some embodiments, the diameter (or width) of each of the electrodes E11-E19, E21-E29, and E31-E39 ranges from about 50 µm, 100 µm, 150 µm, 200 µm, or 250 µm up to about 500 µm, about 1000 µm, about 1500 µm, or about 2000 µm.

The electrode array 120 can be formed in any geometric shape such as a square shape, rectangular shape, or circular shape. Typically the size of the electrode array 120 will be on the order of about 0.1 mm to about 2 cm, wide or in diameter, depending in part on the number of electrodes in the electrode array 120. In various embodiments, the length of the electrode array 120 ranges from about 0.01 mm, or 0.1 mm up to about 10 cm or greater.

One or more of the traces 130 is connected to each of the electrodes E11-E19, E21-E29, and E31-E39. Referring to FIG. 2, in the embodiment illustrated, two traces "T1" and "T2" are connected to each of the electrodes E11-E19, E21-E29, and E31-E39. In alternate embodiments, more than two traces 130 may be connected to each of the electrodes E11-E19, E21-E29, and E31-E39. Connecting more than one of the traces 130 to each of the electrodes E11-E19, E21-E29, and E31-E39 helps ensure signals reach each of the electrodes E11-E19, E21-E29, and E31-E39. In other words, redundancy may be used to improve reliability. For each of the electrodes E11-E19, E21-E29, and E31-E39, the traces 130 are connected to each of the contacts 220 of the electrode and carry signals thereto. Openings 132 (see FIG. 3) formed (e.g., etched) in the body portion 110 expose portions of the traces 130.

The traces 130 may be used to selectively deliver electrical signals (e.g., pulsed signals) to the electrodes E11-E19, E21-E29, and E31-E39. In this manner, only a selected one or more of the electrodes E11-E19, E21-E29, and E31-E39 may deliver stimulation to the spinal cord 330 (see FIG. 3). The electrodes E11-E19, E21-E29, and E31-E39 are operably linked by the traces 130 to control circuitry (not shown). The control circuitry (not shown) is configured to select one or more of the electrodes E11-E19, E21-E29, and E31-E39 to activate/stimulate and/or to control the parameters (e.g., frequency, pulse width, amplitude, and the like) of the electrical stimulation. In various embodiments, the electrode selection, frequency, amplitude, and pulse width are independently selectable. For example, at different times, different electrodes can be selected. At any time, different electrodes can provide stimulation having different parameter values (e.g., frequencies, amplitudes, and the like). In various embodiments, at least a portion of the electrodes may be operated in a monopolar mode and/or a bipolar mode. In such embodiments, constant current or constant voltage may be used to deliver the stimulation.

In some embodiments, the traces 130 may receive signals from implantable control circuitry (not shown) and/or an implantable power source (not shown). The implantable control circuitry (not shown) may be programmed and/or reprogrammed by an external device (e.g., using a handheld device that communicates with the control circuitry through the skin). The programming may be repeated as often as necessary.

FIG. 3 illustrates a cable system 300 incorporating the assembly 100. The cable system 300 is illustrated implanted along the spine 320 and spinal cord 330 of the rat 500 (see FIG. 5A). Due to the difficulty preventing infection at connectors that cross the skin (not shown), in chronic experiments, it is often highly desirable to pass signals through a headplug 310 positioned on the head (not shown) of the rat 500, where the large bone surface, lack of muscle tissue, and minimal movement of skin help minimize the risk of infection. Because some preliminary experiments in living animals have shown that mechanical strains imposed by the animals' movements might make some embodiments of an all-MEMS device configured to extend from the headplug 310 to the spinal cord 330 unreliable, the cable system 300 was devised to confine strain imposed on the assembly 100 to acceptable limits.

FIG. 3 illustrates how the cable system 300 (including the assembly 100) is positioned along the spine 320 of the subject (e.g., the rat 500 illustrated in FIG. 5A) after implantation. The cable system 300 is composed of a spinal baseplate 340, a wire bundle 350, and the headplug 310. Another set of wires (not shown) may be implanted in the leg(s) 520 (see FIG. 5A) of the subject to record electromyography ("EMG") signals. The baseplate 340 may be constructed from a standard FR-4 PCB substrate. The baseplate 340 is attached (e.g., by a suture 342) to a selected vertebrae (e.g., vertebrae "L2"). In the embodiment illustrated, the baseplate 340 is attached to the "L2" vertebrae. The assembly 100 is attached (e.g., by a suture 344) to the spinal cord 300. In the embodiment illustrated, the distal end portion 112 of the assembly 100 is attached to the spinal cord 300 at a location adjacent vertebrae "T13." The proximal end portion 114 of the assembly 100 is attached to the baseplate 340 using a conductive material (e.g., conductive epoxy) to bridge electrical connections. By way of a non-limiting example, the proximal end portion 114 of the assembly 100 may be secured to the baseplate 340 using Loctite M-121 HP Medical device epoxy.

The wire bundle 350 includes a plurality of wires 352. By way of a non-limiting example, the wires 352 may include a different wire for each of the electrodes E11-E19, E21-E29, and E31-E39 (e.g., 27 wires total for a 9×3 array of electrodes). Each of the wires 352 may be constructed from gold and include a Teflon coating. For example, 75 µm gold wires (e.g., Teflon coated gold wire manufactured by AM Systems) may be used. The wires 352 may be soldered to the baseplate 340 and connected by high density connectors 360 to the headplug 310. The traces 130 are connected to the baseplate 340 via the openings 132 formed in the body portion 110 of the assembly 100. By way of a non-limiting example, silver epoxy (not shown) may be used to connect the traces 130 to the baseplate 340.

The entire cable system 300 (except a portion 368 of the assembly 100) may be coated with a coating 370 configured to insulate electrical connections and provide mechanical strength while retaining the flexibility wherever necessary. By way of a non-limiting example, the coating 370 may include a biomedical grade epoxy and a silicone elastomer (e.g., MDX 4-4210 Biomedical grade silicone).

A silicone cap 380 (or overhanging portion) is formed on the end of the baseplate 340 to protect the assembly 100 from external moving tissue. The cap 380 may be formed from the same material as the coating 370. Along portions of the assembly 100, the coating 370 may be implemented as a thin layer of silicone (e.g., about 100 µm thick) to reduce stress concentration as the assembly 100 bends with the subject's spine 320 during movement. A thicker layer of silicone applied to the assembly 100 may be detrimental to the health of the spinal cord 330 because of increased pressure that is applied by a more rigid assembly to the spinal cord. In other words, flexibility may be an important feature of a successful chronic implantable electrode array assembly.

Fabrication

The assembly 100 may be fabricated using a method somewhat similar to that described in D. C. Rodger, et al., "Flexible microfabricated parylene multielectrode arrays for retinal stimulation and spinal cord field modulation," Proc. 4th Inter-

*national IEEE-EMBS Special Topic Conference on Microtechnologies in Medicine and Biology*, Okinawa, Japan, pp. 31-34 (2006), which describes a method of forming a sandwich-like structure of parylene-metal-parylene.

Turning to FIGS. 4A-4D, the assembly 100 may be constructed using a method 400. For ease of illustration, the method 400 will be described with respect to using parylene-C, which is substantially electrically nonconductive. Parylene-C is a United States Pharmacopeial Convention ("USP") class VI biocompatible material, and its mechanical properties provide the necessary flexibility to make good epidural contact with the spinal cord 330 (see FIG. 3). However, those of ordinary skill in the art appreciate that other materials may be used instead of or in combination with parylene-C. Examples of other materials include flexible materials such as parylene-A, parylene-AM, parylene-F, parylene-N, parylene-D, and the like. Further, the electrode arrays 120 will be described as including metal, which may be implemented using one or more biocompatible metals (e.g., gold, platinum, chromium, titanium, iridium, tungsten, and/or oxides and/or alloys thereof). For ease of illustration, the method 400 will be described with respect to using platinum (and titanium) to construct the electrode arrays 120.

Figure 4A:
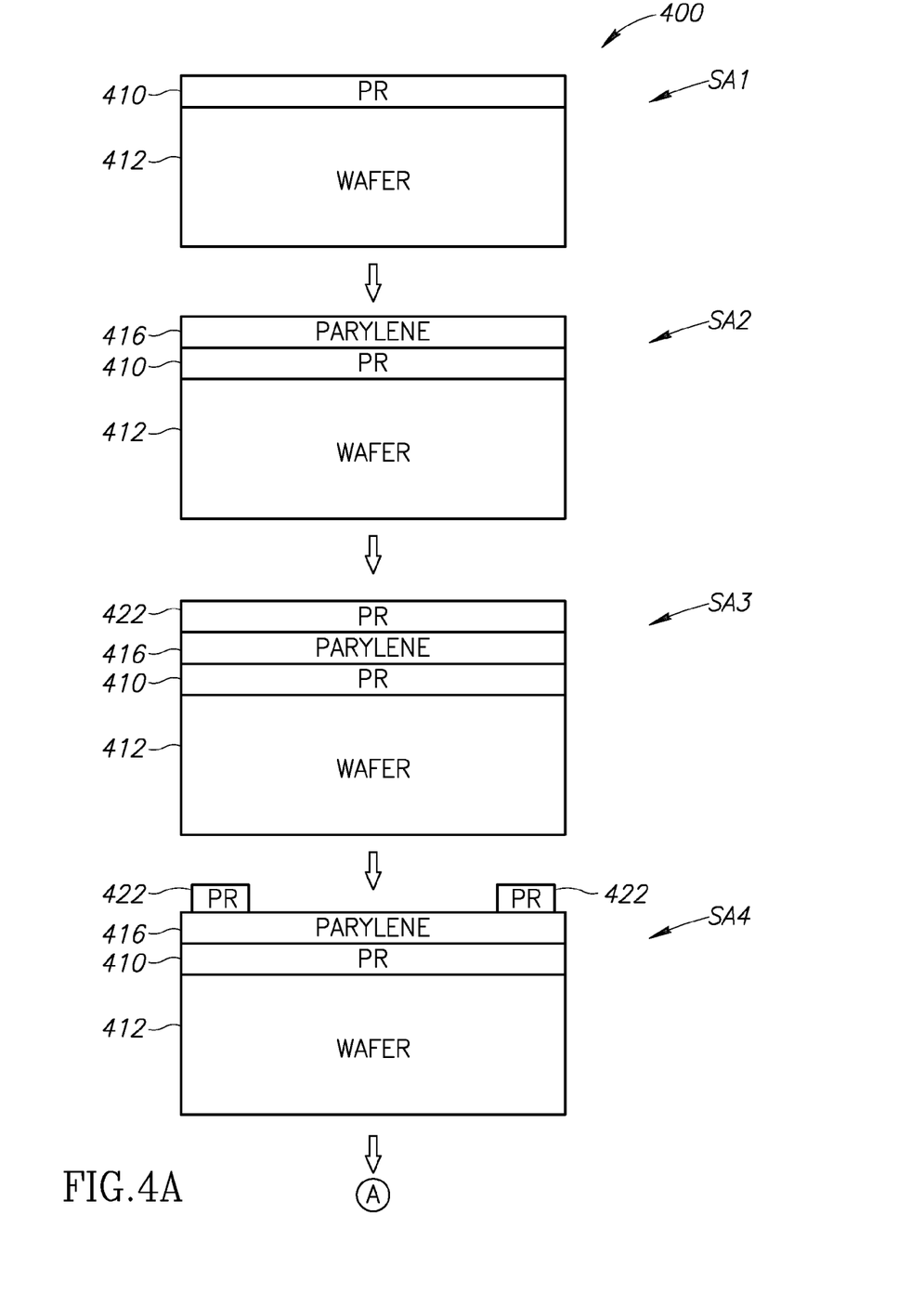
FIG. 4A is an illustration of a first portion of a method of constructing the assembly of FIG. 1.

The method 400 begins at the top of FIG. 4A. A first subassembly "SA1" is constructed by applying (e.g., spinning) an optional first layer of sacrificial photoresist 410 on a substrate 412 (e.g., a silicon wafer).

Then, a second subassembly "SA2" is constructed by depositing (e.g., using conventional vapor-deposition) a first (frame) layer of parylene-C 416 on the first layer of photoresist 410. By way of a non-limiting example, the first (frame) layer of parylene-C 416 may be about 10 µm thick.

A third subassembly "SA3" is constructed by applying (e.g., spinning) a second layer of photoresist 422 on the second subassembly "SA2."

Next, a fourth subassembly "SA4" is constructed by exposing and developing the second layer of photoresist 422 to define the frame 140 (see FIG. 1) using conventional photoresist techniques.

Figure 4B:
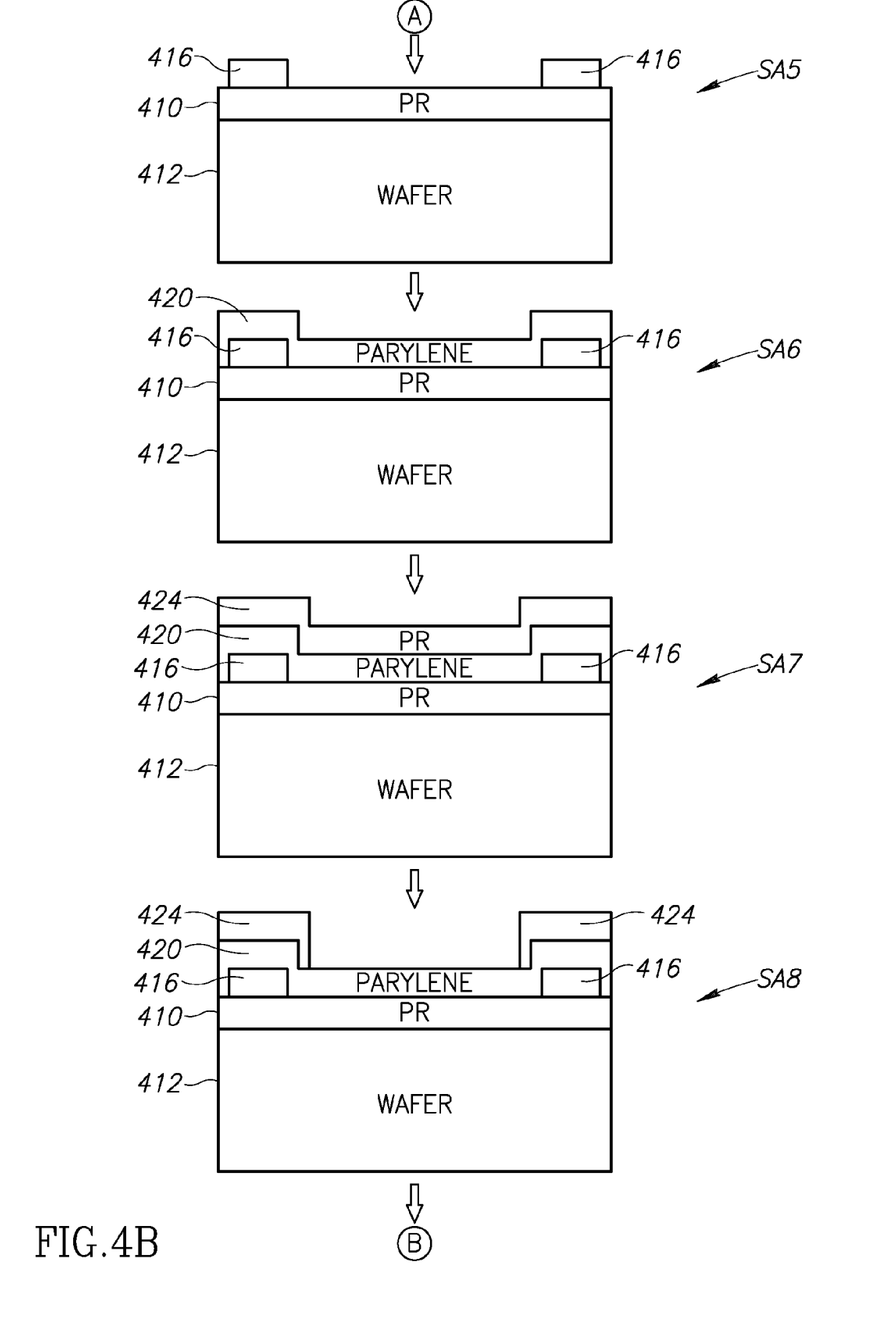
FIG. 4B is an illustration of a second portion of the method of constructing the assembly of FIG. 1.

Turning to FIG. 4B, a fifth subassembly "SA5" is constructed by removing (e.g., etching) at least a portion of the first (frame) layer of parylene-C 416 to define the at least a portion of the frame 140 that surrounds the electrode array 120. Then, the second layer of photoresist 422 is removed (e.g., dissolved using acetone).

Next, a sixth subassembly "SA6" is constructed by depositing (e.g., using conventional vapor-deposition) a second (base) layer of parylene-C 420 on the fifth subassembly "SA5." By way of another non-limiting example, the second (base) layer of parylene-C 420 may be about 5 µm thick. The second (base) layer of parylene-C 420 forms an underside for the body portion 110 (see FIG. 1) of the assembly 100 (see FIG. 1). The second (base) layer of parylene-C 420 may also be characterized as defining at least a portion of the frame 140 because the first (frame) layer of parylene-C 416 is underneath and helps shape the second (base) layer of parylene-C 420. In other words, the frame 140 may be characterized as including both first (frame) and the second (base) layers 416 and 420. Alternatively, the frame 140 may be characterized as being defined entirely by the first (frame) layer 416.

A seventh subassembly "SA7" is constructed by applying (e.g., spinning) a third layer of photoresist 424 onto the sixth subassembly "SA6."

An eighth subassembly "SA8" is constructed by exposing and developing the third layer of photoresist 424 to define a pattern using conventional photoresist techniques. The pattern defines the electrode array 120 and the traces 130.

Figure 4C:
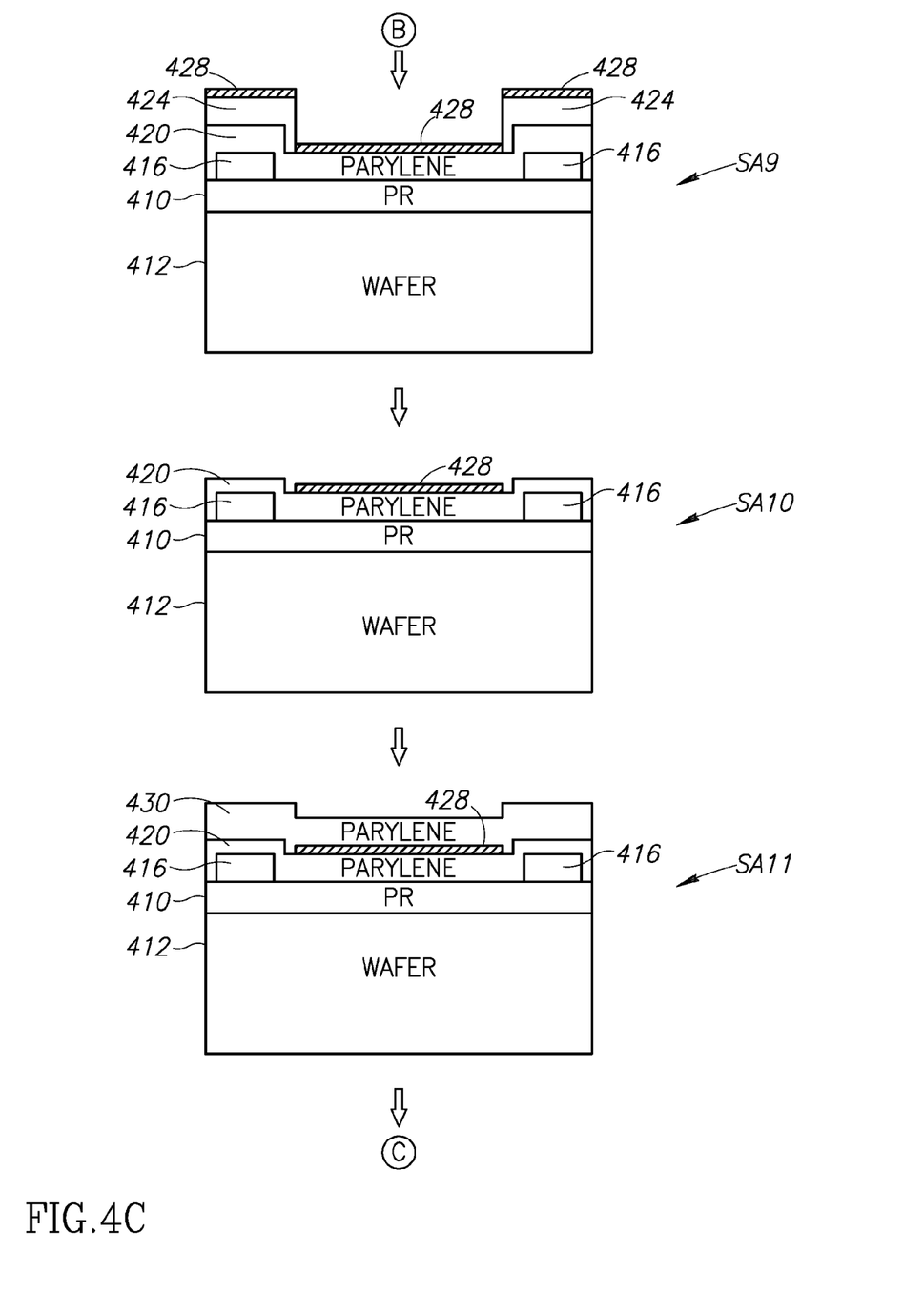
FIG. 4C is an illustration of a third portion of the method of constructing the assembly of FIG. 1.

Turning to FIG. 4C, a ninth subassembly "SA9" is constructed by depositing (e.g., using ebeam evaporation) an electrically conductive layer 428 on the eighth subassembly "SA8." The electrically conductive layer 428 may be constructed by first depositing an adhesion layer of a first material (e.g., 100 Å of titanium) and then depositing an electrode layer of a second different electrically conductive material (e.g., 2000 Å of platinum) suitable for conducting electrical stimulation. Thus, the electrically conductive layer 428 may be constructed using more than one layer of material.

A tenth subassembly "SA10" is constructed by removing (e.g., dissolving) the third layer of photoresist 424, which removes portions of the electrically conductive layer 428 positioned thereupon to form the electrode array 120 and the traces 130. In other words, a conventional liftoff process is used to pattern the electrically conductive layer 428 to form the electrode array 120 and the traces 130.

Next, an eleventh subassembly "SA11" is constructed by depositing (e.g., using conventional vapor-deposition) a third (top) layer of parylene-C 430 on the tenth subassembly "SA10." By way of another non-limiting example, the third (top) layer of parylene-C 430 may be about 5 µm thick.

Figure 4D:
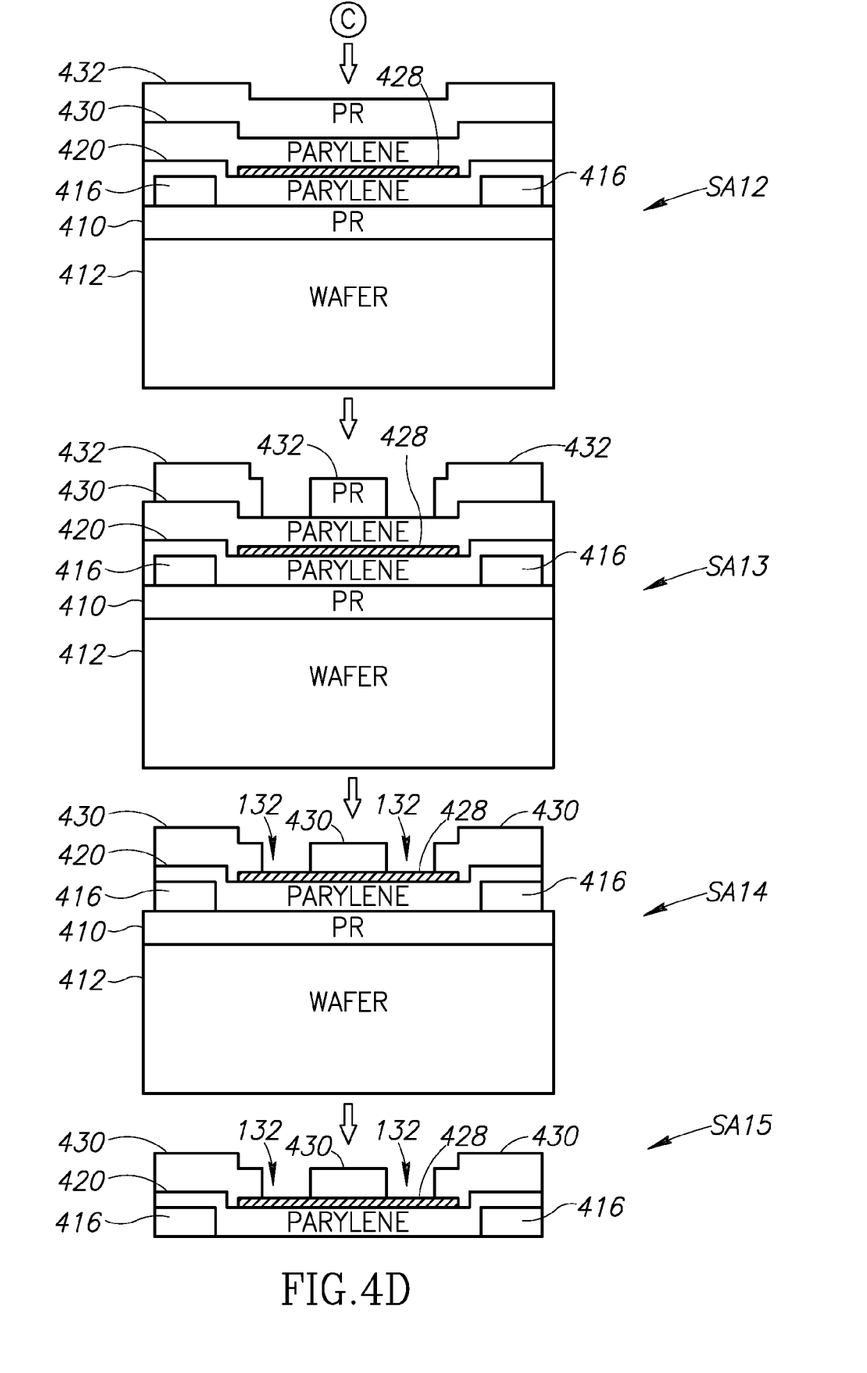
FIG. 4D is an illustration of a fourth portion of the method of constructing the assembly of FIG. 1.

Turning to FIG. 4D, a twelfth subassembly "SA12" is created by applying (e.g., spinning) a fourth layer of photoresist 432 onto the eleventh subassembly "SA11."

A thirteenth subassembly "SA13" is constructed by exposing and developing the fourth layer of photoresist 432 to define a pattern using conventional photoresist techniques. The pattern defines the openings 132, which are formed in the third (top) layer of parylene-C 430.

A fourteenth subassembly "SA14" is created by forming the openings 132 in the third (top) layer of parylene-C 430 to expose portions of the electrically conductive layer 428. The openings 132 may be formed using etching (e.g., oxygen plasma etching). For each of the electrodes E11-E19, E21-E29, and E31-E39, at least a portion of the openings 132 provide access to the contacts 220 and define the grid structure 210. The contacts 220 contact the spinal cord 330 (see FIG. 3) through the openings 132. A different portion of the openings 132 provide access to the traces 130 so that the baseplate 340 may be electrically connected thereto. Etching may also be used to define the shape of the assembly 100. Then, the fourth layer of photoresist 432 is removed (e.g., dissolved using acetone or water).

A fifteenth subassembly "SA15" is formed by removing (e.g., dissolving) the first layer of photoresist 410 to release the layers above the first layer of photoresist 410 from the substrate 412. By way of a non-limiting example, the first layer of photoresist 410 may be dissolved using acetone or water.

Finally, the assembly 100 (see FIG. 1) may be created by annealing the fifteenth subassembly "SA15" in a vacuum oven at 200° C. for 48 hours.

Results and Discussion

Implementations of the cable system 300 (see FIG. 3) were implanted in rats and functioned for up to eight weeks. This level of reliability makes the cable system 300 (and assembly 100) suitable for studying stepping ability over time. The cable system 300 (and assembly 100) also provides site selectivity, afforded by the high density microfabricated electrode array 120.

Figure 5B:
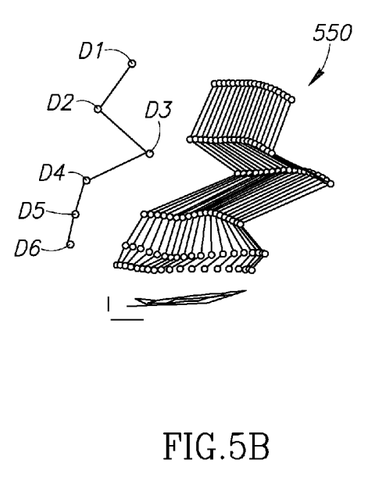
FIG. 5B is a stick diagram illustrating a dragging motion of the hindlimb of the rat on the treadmill when no stimulation is applied to the rat's spinal cord by the assembly of FIG. 1.

FIG. 5A is an illustration of the rat 500 suspended over a treadmill 510 by a jacket 530. The rat 500 has a completely transected spinal cord and thus hindlimb paralysis. Stepping by the hind limbs was achieved in the rat 500 by stimulating the rat's spinal cord 330 (see FIG. 3) while with the rat was suspended over the treadmill 510. FIG. 5A also illustrates portions of a motion capture system (e.g., dots D1-D5) used to record stepping ability. FIG. 5B is a stick diagram 550 representing hind limb motion when the rat's spinal cord 330 was not stimulated. As expected, the rat 500 dragged its feet when its spinal cord 330 was not stimulated due to the hindlimb paralysis.

Figure 6A:
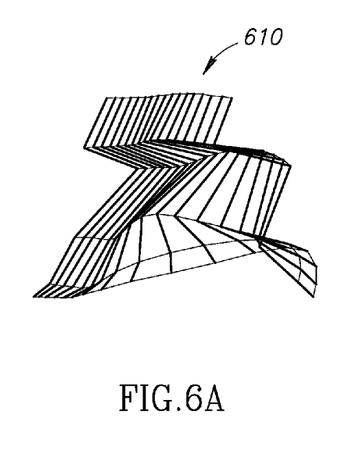
FIG. 6A is a stick diagram illustrating hind limb motion when bipolar stimulation was applied to the rat's spinal cord by a first pair of electrodes of the assembly of FIG. 1.
Figure 6B:
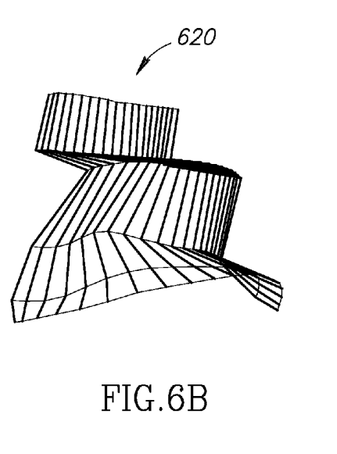
FIG. 6B is a stick diagram illustrating hind limb motion when bipolar stimulation was applied to the rat's spinal cord by a second different pair of electrodes of the assembly of FIG. 1.

FIGS. 6A and 6B depict a pair of stick diagrams 610 and 620, respectively, that illustrate hind limb motion when bipolar stimulation is applied to the rat's spinal cord 330 by two different electrode pairs. The diagrams 610 and 620 are believed to illustrate the first stepping achieved by a spinalized rat stimulated by a MEMS electrode array. Of note is that the stimulation site pairs for the two different stepping patterns illustrated in FIGS. 6A and 6B were close together in the electrode array 120, suggesting that the high-density electrode configuration of the assembly 100 is of great value in understanding the biological mechanisms underlying locomotion and its application to recovery after spinal cord injury.

Figure 7A:
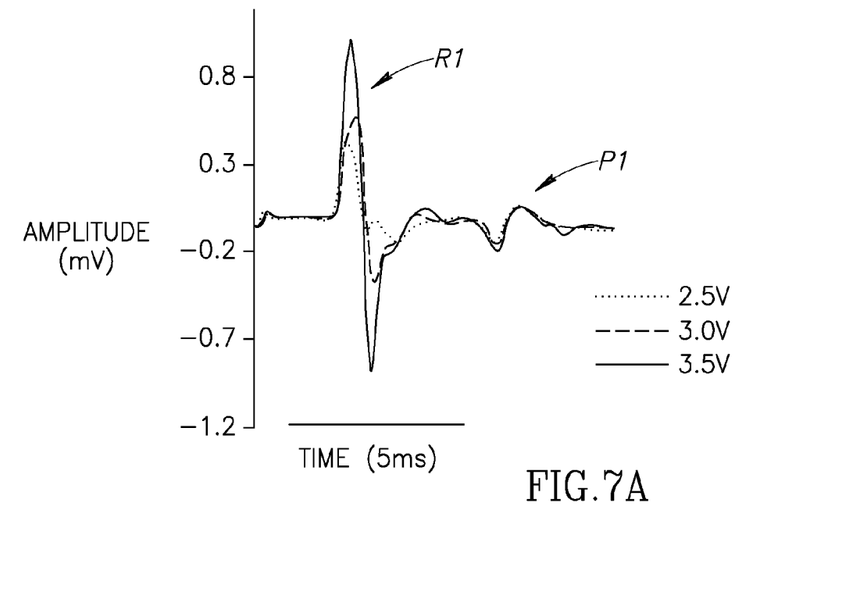
FIG. 7A is a graphical representation of an electromyography ("EMG") recording recorded when bipolar stimulation was applied to the rat's spinal cord by a first pair of electrodes of the assembly of FIG. 1.
Figure 7B:
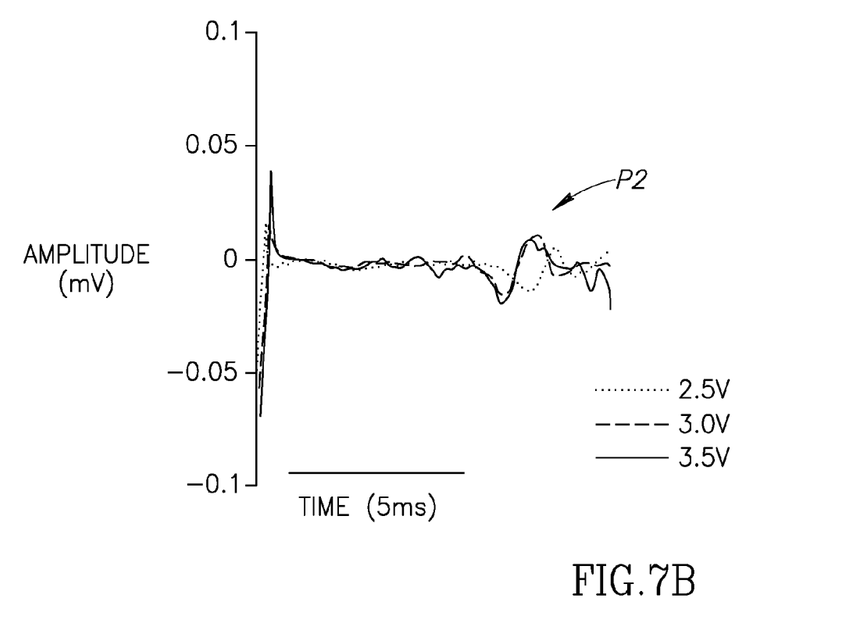
FIG. 7B is a graphical representation of an EMG recording recorded when bipolar stimulation was applied to the rat's spinal cord by a second different pair of electrodes of the assembly of FIG. 1.

EMG recording may also be very valuable in obtaining biological information. FIGS. 7A and 7B show two EMG recordings for two different stimulation pairs at three different voltages. In other words, FIG. 7A depicts an EMG recording recorded when stimulation was applied by one pair of electrodes and FIG. 7B depicts an EMG recording recorded when stimulation was applied by a different pair of electrodes. FIG. 7A illustrates a monosynaptic response "R1." Such monosynaptic responses generally occur in the first six milliseconds of the recordings, while polysynaptic responses (such as polysynaptic responses "P1") generally occur later. Of note is that the recording depicted in FIG. 7A includes both the monosynaptic response "R1" and the polysynaptic responses "P1," while the recording depicted in FIG. 7B includes only polysynaptic responses "P2." This demonstrates that the high density of electrode array 120 provides high-density stimulation sites (the electrodes E11-E19, E21-E29, and E31-E39) that are useful in eliciting different biological responses. The EMG signals of FIGS. 7A and 7B were obtained during reflex tests (0.3 Hz stimulation pulses), and the stick diagrams of FIGS. 6A and 6B were obtained during stepping testing (40 Hz).

The assembly 100 has been shown to survive in a living rat for up to eight weeks and may survive much longer, because the impact of mechanical damage observed on the functionality of the assembly 100 is minimal. The cable system 300 provides a means for stimulating the spinal cord 330 and recording evoked responses. Optionally, the electrodes E11-E19, E21-E29, and E31-E39 of the assembly 100 may be used to detect neurological signals in addition to delivering stimulation. The stimulation applied by the assembly 100 may be used to induce stepping in a rat with a completely transected spinal cord. The assembly 100 provides a means for controlling the site of stimulation to produce different EMG responses and stepping patterns. This level of control is useful for understanding neurobiological circuits inside the spinal cord 330 and developing possible treatments for locomotion recovery in victims of spinal cord injury.

While the cable system 300 including the assembly 100 has been described with respect to enabling stepping in a subject (e.g., the rat 500), through application of ordinary skill in the art to the present teachings embodiments can be constructed that enable other types of functionality, such as to (a) enable voluntary movement of muscles involved in at least one of standing, stepping, reaching, grasping, voluntarily changing positions of one or both legs, voiding the bladder, voiding the bowel, postural activity, and locomotor activity; (b) enable or improve autonomic control of at least one of cardiovascular function, body temperature, and metabolic processes; and/or (c) help facilitate recovery of at least one of an autonomic function, sexual function, vasomotor function, and cognitive function.

All publications, patents, and patent applications cited herein are hereby incorporated by reference in their entireties for all purposes.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. An implantable device for use with a spinal cord, the device comprising:
a body portion having a peripheral portion and a first layer constructed from a substantially electrically nonconductive material, the first layer having a first portion and a second portion, the first portion being positionable alongside the spinal cord and comprising a first plurality of openings, the second portion comprising a second plurality of openings;
a plurality of electrodes positioned inside the peripheral portion and alongside the first portion of the first layer, at least one of the first plurality of openings being adjacent each of the electrodes to provide a pathway through which the electrode may provide electrical stimulation to the spinal cord when the first portion is positioned alongside the spinal cord and wherein the at least one of the first plurality of openings adjacent each of the plurality of electrodes comprise more than one opening;
a plurality of traces positioned inside the peripheral portion and alongside the first layer with at least one of the second plurality of openings being adjacent each of the traces to provide a pathway through which the trace may receive electrical stimulation, one or more of the traces being connected to each of the electrodes and configured to conduct electrical stimulation received by the one or more of the traces to the electrode; and
a plurality of grid structures positioned inside the first layer with a different one of the grid structures being adjacent each of the plurality of electrodes, each grid structure comprises a plurality of cells, for each of the plurality of electrodes, each of the at least one of the first plurality of openings adjacent the electrode being positioned inside a different one of the cells of the grid structure adjacent the electrode.

2. The device of claim 1, wherein the plurality of traces is configured to conduct different electrical stimulation to different ones of the plurality of electrodes.

3. The device of claim 1, wherein the plurality of traces is configured to conduct electrical stimulation to fewer than all of the plurality of electrodes.

4. The device of claim 1, wherein the first portion of the first layer is positionable against a dura of the spinal cord and the plurality of electrodes are configured to provide electrical stimulation to the dura.

5. The device of claim 1, wherein the peripheral portion comprises a frame positioned adjacent the first layer.

6. The device of claim 1, wherein the one or more of the traces connected to each of the electrodes comprises two traces.

7. The device of claim 1, wherein the body portion further comprises a second layer, the plurality of electrodes and the plurality of traces being positioned between the first and second layers.

8. The device of claim 7, further comprising:
a flexible outer coating that coats at least a portion of the second layer of the body portion and a portion of the first layer between the first portion of the first layer and the second portion of the first layer.

9. The device of claim 8, wherein the outer coating comprises at least one of a biomedical grade epoxy and a silicone elastomer.

10. The device of claim 7, wherein the first and second layers are each constructed from at least one of parylene-A, parylene-C, parylene-AM, parylene-F, parylene-N, and parylene-D.

11. The device of claim 1, wherein the first layer is constructed from at least one of parylene-A, parylene-C, parylene-AM, parylene-F, parylene-N, and parylene-D.

12. An implantable device for use with a spinal cord, the device comprising:
a substantially electrically nonconductive first layer having a first portion positionable alongside the spinal cord comprising a first plurality of openings and a second portion comprising a second plurality of openings;
a body portion having a peripheral portion comprising a plurality of electrodes and a plurality of traces positioned inside the peripheral portion and alongside the first layer, at least one of the first plurality of openings being adjacent each of the electrodes comprising more than one opening and providing a pathway through which the electrode may provide electrical stimulation to the spinal cord;
at least one of the second plurality of openings being adjacent each of the traces to provide a pathway through which the trace may receive electrical stimulation, one or more of the traces being connected to each of the electrodes and configured to conduct electrical stimulation received by the one or more of the traces to the electrode; and
a plurality of grid structures positioned inside the first layer with a different one of the grid structures being adjacent each of the plurality of electrodes and comprising a plurality of cells, for each of the plurality of electrodes, each of the at least one of the first plurality of openings adjacent the electrode being positioned inside a different one of the cells of the grid structure adjacent the electrode.

13. The device of claim 12, wherein the plurality of traces is configured to conduct different electrical stimulation to different ones of the plurality of electrodes.

14. The device of claim 12, wherein the plurality of traces is configured to conduct electrical stimulation to fewer than all of the plurality of electrodes.

15. The device of claim 12, wherein the first portion of the first layer is positionable against a dura of the spinal cord and the plurality of electrodes are configured to provide electrical stimulation to the dura.

16. The device of claim 12, wherein the peripheral portion comprises a frame positioned adjacent the first layer.

17. The device of claim 12, wherein the one or more of the traces connected to each of the electrodes comprises two traces.

18. The device of claim 12, wherein the body portion further comprises a second layer, the plurality of electrodes and the plurality of traces being positioned between the first and second layers.

19. The device of claim 12, further comprising:
a flexible outer coating that coats at least a portion of the second layer of the body portion and a portion of the first layer between the first portion of the first layer and the second portion of the first layer.

20. The device of claim 19, wherein the outer coating comprises at least one of a biomedical grade epoxy and a silicone elastomer.

21. The device of claim 18, wherein the first and second layers are each constructed from at least one of parylene-A, parylene-C, parylene-AM, parylene-F, parylene-N, and parylene-D.

* * * * *